United States Patent
Min et al.

[11] Patent Number: 5,916,587
[45] Date of Patent: Jun. 29, 1999

[54] TRANSDERMAL DELIVERY MATRIX FOR PIROXICAM

[75] Inventors: Dong Son Min, Seoul; Kee An Um; Yong Soo Kim, both of Kyungki-do; Pyeong Uk Park, Seoul; Key Hyup Kim, Seoul; Ho Seung Yang, Seoul; Hey Soon Jeong; Mi Young Park, both of Kyungki-do, all of Rep. of Korea

[73] Assignee: Sunkyong Industries Co., Ltd., Rep. of Korea

[21] Appl. No.: 08/943,140

[22] Filed: Oct. 3, 1997

Related U.S. Application Data

[63] Continuation of application No. 08/454,379, filed as application No. PCT/KR93/00127, Dec. 31, 1993, abandoned.

[30] Foreign Application Priority Data

Dec. 31, 1992 [KR] Rep. of Korea ............ 92-27130

[51] Int. Cl.⁶ ............................................. A61F 13/02
[52] U.S. Cl. ................................ 424/448; 424/449
[58] Field of Search ............................. 424/449, 448

[56] References Cited

U.S. PATENT DOCUMENTS

| | | | |
|---|---|---|---|
| 4,557,934 | 12/1985 | Cooper | 424/128 |
| 4,758,434 | 7/1988 | Kydonieus | 424/449 |
| 4,900,554 | 2/1990 | Yanagibashi et al. | 424/448 |
| 4,906,475 | 3/1990 | Kim | 424/449 |
| 5,032,403 | 7/1991 | Sinnreich | 424/448 |
| 5,082,866 | 1/1992 | Wong | 514/785 |
| 5,133,972 | 7/1992 | Ferrini | 424/449 |
| 5,196,410 | 3/1993 | Francoeur et al. | 514/159 |
| 5,234,957 | 8/1993 | Mantelle | 514/772.6 |
| 5,262,165 | 11/1993 | Govil | 424/448 |

*Primary Examiner*—D. Gabrielle Brouillette
*Attorney, Agent, or Firm*—Finnegan, Henderson, Farabow, Garrett & Dunner, L.L.P.

[57] ABSTRACT

The present invention is directed to a pharmaceutical compositions improving percutaneous absorbability by absorption assistants, which remarkably increase permeation and dissolution of piroxicam, and penetration enhancers. A further surprising feature of the present invention resides in the fact that absorption assistant which assists penetration enhancer is able to include the active substance excessively in adhesive matrix as solvent of the active substance.

6 Claims, 1 Drawing Sheet

- ○: REFERENCE GROUP
- ▲: TOPICAL APPLIED PATCH (5mg/kg)
- ■: SYSTEMICAL APPIED PATCH (30mg/kg)

TRANSDERMAL DELIVERY MATRIX FOR PIROXICAM

This is a continuation of application Ser. No. 08/454,479, filed Aug. 29, 1995, now abandoned, which is a §371 application of PCT/KR93/00127, filed Dec. 31, 1993.

BACKGROUND OF THE INVENTION

The present invention is directed to a transdermal (or percutaneous) delivery system for piroxicam. This delivery system is a drug-containing adhesive device which has a constant release rate over a period of time.

Piroxicam is a non-steroidal anti-inflammatory drug and used as an effective analgesic and anti-inflammatory agent in rheumatoid arthritis, osteoarthritis and acute pain in musculoskeletal disorders and acute gout. It has been known to be an effective analgesic in fracture, dental, postoperative and postpartum pain. It is about equal in potency to indomethacin as an inhibitor of prostaglandin biosynthesis in vitro.

Piroxicam is used generally orally. Although piroxicam has a strong therapeutic effect, it causes side effects such as gastro-intestinal trouble, peptic ulcer. Orally administered piroxicam is metabolized at the first pass route. Less than 5% of the drug is excreted in the urine unchanged. The metabolite is at least 1000 times less active than piroxicam inhibiting prostaglandin synthesis.

The potential advantage of delivering piroxicam transdermally is that gut wall and hepatic metabolism and the gastrointestinal reaction may be avoided.

Transdermal delivery system eliminates the first pass effects and allows a controlled amount of the active substance such as piroxicam to be continuously administered over a sustained period of time.

Francoeur et al., U. S. patent application Ser. No. 925, 641(Oct. 31, 1986), disclose topical compositions of amlodipine, doxazosin, glipizide, piroxicam and other drugs containing aqueous solution of ethanol, 1-alkylazacycloheptane-2-one and oleic aicd. However, this method is impossible to make a thin patch and is only possible to make gel, ointment and liquid compositions.

In Japanese, Laid-Open Patent Ser. No. 91-251534, there is disclosed patch compositions for increased dermal penetration of piroxicam by adding penetration enhancer, selected from polyoxyethylenealkyl ethers or alkanolamides, and dissolving assitant agent of polyvinypyrrolidone to pressure-sensitive adhesives of copolymer of vinylpyrrolidone and methacrylic ester. However, this composition is also inferior in percutaneous absorption because polyvinylpyrrolidone of dissolving agent acts only a dissolving assistant role and does not assist the absorption of drug.

For the reasons mentioned above, as result of concentrative researches about the improvement of percutaneous absorption and high content of drug in patch, the present inventors found that, in case of using certain absorption assitants, the excessively dissolved piroxicam is included in matrix and simultaneously the percutaneous absorbability is surprisingly enhanced, so that have been perfected the present invention.

SUMMARY OF THE INVENTION

The present invention is related to transdermal drug delivery system. The transdermal delivery system is preferably used to administer piroxicam with corticosteroid for the treatment of rheumatoid arthritis, osteoarthritis, acute pain in musculoskeletal disorder and acute gout.

The present invention is directed to a transdermal delivery system improving percutaneous absorbability by absorption assistants, which remarkably increase permeation and dissolution of piroxicam, and penetration enhancers. A further surprising feature of the present invention resides in the fact that absorption assistant which assists penetration enhancer is able to include the active substance excessively in adhesive matrix as solvent of the active substance.

The system comprises a matrix which is sandwiched between a release liner on a backing layer. The matrix consists of one or several laminated layer to be controlled by a active substance release rate which comprises on a weight percentage basis, from about 35 to about 90% of an adhesive polymer, from about 9 to about 40% of absorption assistants which maintain the active substance in a solubilized state in the polymer, from about 0.5 to about 10% of penetration enhancer and from about 0.5 to about 25% of the active substance.

DETAILED DESCRIPTION OF THE DRAWINGS

DETAILED DESCRIPTION OF THE INVENTION

Figure 1:
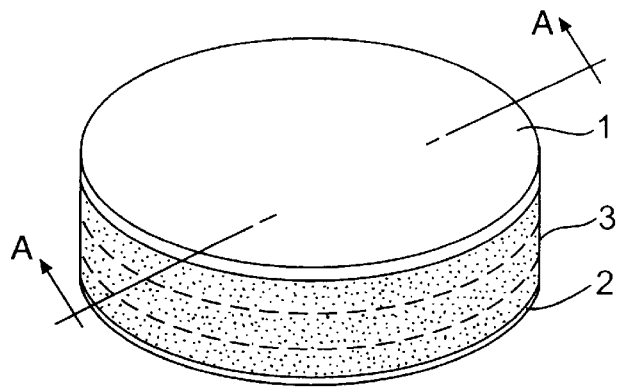
FIG. 1 is an isometric view of a preferred embodiment of the present invention.
Figure 2:
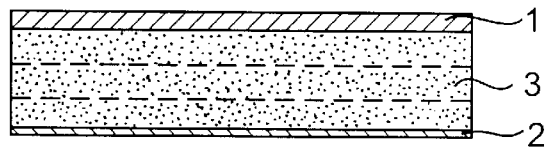
FIG. 2 is a sectional view taken generally along lines A—A in FIG. 1.

In the present invention, the transdermal delivery system comprises an impermeable backing membrane(1), a polymeric diffusion matrix(3) which preferably found by one or more thin layer (illustrated in phantom) and a release liner(2). The impermeable backing membrane is well known in the art and is not limiting on the instant invention.

The matix is compounded on a weight percentage basis, from about 35 to 90% of an adhesive polymer, from about 9 to about 40% of absorption assistants which maintain the piroxicam in a solubilized state, from about 0.5 to about 10% of penetration enhancer and from about 0.5 to about 25% of the active substance.

The adhesive polymer is a pressure sensitive adhesive and is acceptable for medical use. Of these type of polymer, either water base or solvent base materials may be used. These polymers have two functions in the instant invention. First, they are adhesive to the skin and securely hold the matrix on and in good diffusion contact with the skin. Second, they are the carrier of the active substance or storage of the active substance.

Preferably, the adhesive polymer is a vinylacetate-acrylate multipolymer. Such a multipolymer is commercially available from the Monsanto Company, St. Louise 70. under the name of GELVA®, GELVA®737, 788 and 2484 may be used. Specifically, GELVA®737 comprises up to 1.1% of 2-ethylhexyl acrylate and the balance vinyl acetate.

The active substance which is transdermally delivered to the systemic circulation of the body in therapeutically effective amount is preferably piroxicam.

To produce the synergistic effect locally; from about 0.5 to about 15.0% of a corticosteroid is added to the polymer matrix. Such a corticosteroid is one or more selected from the group of cortisone, hydrocortisone, prednisolone, dexamethasone and their derivatives.

The solvent, absorption assistant, dissolves the active substances. The solvent is one or more selected from the group of dimethyl sulfoxide, dimethyl acetamide, dimethyl formamide, polyethylene glycol, propylene glycol, polyoxyethylene ester, alkanolamine, alkylamine, N-alkyl pyrrolidone and diethylene glycol mono ethyl ether. The skin penetration enhancer is one or more selected from the group of propylene glycol, 1-dodecylazacycloheptane-2-one, oleic acid, fatty acid alkanolamide such as lauric diethanolamide and polyethylene glycol derivatives such as polyethylene glycol 200 mono laurate, polyethylene glycol 300 mono laurate, polyethylene glycol 400 mono laurate and so on.

In operation, the system is applied to the skin where the adhesive polymer affixes the system on the skin. The active substance which is dissolved by the solvent, is dispersed throughout the matrix. The active substance diffuses from the matrix with the enhancer. At the stratum comeum, the enhancer facilitates the transdermal diffusion therethrough and into the systemic circulation.

The preparation of the transdermal delivery system according to the present invention is accomplished as follows. The active substance is dissolved in the solvent and enhancer to form a solution or a suspension. This solution or suspension is added to the polymer and mixed for about 20~30 minutes and then allowed to stand for about 20~60 minutes to eliminate the air bubbles. This mixture is cast on the impermeable membrane, a polyethylene film or aluminized polyethylene film made by 3M Company (e.g. 3M-Scotchpak 1006 or 3M 1012) and dried at about 40° C. to 50° C. for about 30~60 minutes. After drying the coated matrix, a release liner, such as a silicon release paper, or the like which are well known, is placed over the exposed surface of the matrix. Then the system is die-cut into a optimum size. If multiple matrix layers are required, each subsequent layer is cast over or overlaps on the previous layer. The finished system is put into a pouch and hermetically sealed.

EXAMPLE 1

To prepare the matrix, 0.4 g of piroxicam is dissolved in 1.0 g of dimethyl sulfoxide and 0.3 g of triethanol amine. 0.3 g of poly ethylene glycol 400 monolaurate and 0.1 g of hydrocortisone are added to the solution and mixed well. This solution is added to 10 g of polymer solution (Mosanto GELVA®737) and then mixed for 20~30 minutes. After mixing, the mixture is settled for about 20 minutes to remove air bubbles and is cast onto the backing material (3M-Scotchpak 1006 or 1012). The cast mixture is dried for 30 minutes at 45° C. To make a triple layer matrix, the 2nd and 3rd layer are sequentially cast over the prior layer after the prior layer is settled and dried or cast the mixture on the release liner and overlay on the prior layer. This formation is then cut into 10 cm$^2$ shapes.

EXAMPLE 2

0.2 g of piroxicam is dissolved in 1.5 g of dimethylacetamide. 0.4 g of lauric diethyanolamide, 0.5 g of polyethylene glycol 200 monolaurate and 0.05 g of prednisolone are added to the solution and mixed well. This solution mixed with 12 g of polymer solution (Mosanto GELVA®788) for 25 minutes.

After settling for 20 minutes, the mixture is cast onto the backing material. The remaining steps are same as set forth in Example 1.

EXAMPLE 3

0.3 g of piroxicam is dissolved in 1.8 g of diethyleneglycol monoethyl ether. 0.5 g of polyethylene glycol 300 monolaurate, 0.2 g of diethanolamine and 0.1 g of hydrocortisone are added to the solution and then mixed well. This solution is mixed with 25 g of polymer solution (Monsanto GELVA®2484) for 20 minutes. The remaining steps are set forth in Example 1.

EXAMPLE 4

0.5 g of piroxicam is dissolved in 3.0 g of dimethylformamide. 0.45 g of polyethyleneglycol 400 monolaurate, 0.1 g of polysorbate 80 and 0.3 g of hydrocortisone are added to the solution and then mixed well. This solution is mixed setling for 20 minutes, the further steps are set forth in Example 1 are followed.

EXAMPLE 5

1.0 g of piroxicam is dissolved in 1.5 g of diethyleneglycol monoethylether. 0.4 g of polyethylene glycol 200 monolaurate, 0.3 g of lauric diethanolamide and 0.2 g of polysorbate 60 are added to the solution and then mixed well. This solution is mixed with 10 g of polymer solution (Monsanto GELVA®737) for 25 minutes. The remaining steps are the same as set forth in Example 1.

EXAMPLE 6

Piroxicam 0.7 g is dissolved in 2.2 g of dimethylsulfoxide and 1.0 g of diethyleneglycol mono ethylether. 0.3 g of lauric diethanolamide, 0.2 g of polysorbate 20 and 0.3 g of hydrocortisone are added to the solution and then mixed throughly. This solution is mixed with 15 g of polymer solution (Monsanto GELVA®737) for 30 minutes. After settling for 20 minutes, the remaining steps are set forth in Example 1.

EXAMPLE 7

0.4 g of piroxicam is dissolved in 0.8 g of dimethylsulfoxide and 1.5 g of diethyleneglycol mono ethylether. 0.05 g of 1-dodecylazacycloheptane-2-one, 0.5g of polyethyleneglycol 200 monolaurate, 0.2 g of polysorbate 80 and 0.1 g of hydrocortisone are added to above solution and is mixed well. This solution is mixed well with 10 g of polymer solution (Monsanto GELVA®737), and then this mixture is cast to 0.6 mm thick onto the backing material—aluminized polyethylene film (3M-Scotchpak 1009) after settled to remove the air bubbles. The casting material is dried for 60 minutes at 45° C. and then the release liner is covered over the dried matrix. This formation is then cut into 20 cm$^2$ shape.

EXAMPLE 8

0.35 g of piroxicam is dissolved in 1.2 g of dimethylsulfoxide, 0.3 g of N-octylpyrroliclone and 0.7 g of diethyleneglycol mono ethylether. 0.4 g of oleic acid, 0.05 g of polysorbate 80 and 0.2 g of lauric diethanolamide are added to the solution and then mixed well. This solution is mixed well with 10 g of polymer solution (Monsanto, GELVA®737), and then this mixture is cast to 0.6 mm thick onto the backing material—aluminized polyethylene film (3M-Scotchpak 1009) after settled to remove the air bubbles. The casting material is dried for 60 minutes at 45° C. To make a double layer matrix, the second layer is cast over the prior dried layer or cast the mixture on the release liner and overlay on the prior layer. This formation is then cut into 20 cm$^2$ shape.

EXAMPLE 9

0.5 g of piroxicam is dissolved in 2.5 g of dimethylsulfoxide, 0.5 g of diethyleneglycol mono ethylether and 0.1 g of N-decylmethylsulfoxide. 0.3 g of lauric diethanolamide, 0.05 g of BHA/BHT mixture (Sustane), 0.05 g of polysorbate 80 and 0.2 g of hydrocortisone are added to above solution and is mixed well. This solution is mixed with 10 g of polymer solution (Monsanto GELVA®737), and then this mixture is settled to remove the air bubbles. The further steps are the same as set forth in Example 8.

EXAMPLE 10

0.4 g of piroxicam is dissolved in 1.8 g of dimethylsulfoxide and 1.5 g of diethyleneglycol mono ethylether. 0.3 g of lauric diethanolamide, 0.5 g of polyethyleneglycol 200 monolaurate, 0.05 g of polysorbate 80 and 0.1 g of hydrocortisone are added to above solution and is mixed well. This solution is mixed well with 11 g of polymer solution (Monsanto GELVA®737), and then this mixture is settled to remove the air bubbles. The remaining steps are the same as set forth in Example 8.

EXAMPLE 11

1.0 g of piroxicam is dissolved in 1.8 g of dimethylsulfoxide and 0.5 g of diethyleneglycol mono ethylether. 0.4 g of oleic acid, 0.05 g of polysorbate 80 and 0.1 g of hydrocortisone are added to above solution and this solution is mixed well. This solution is mixed well with 15 g of polymer solution (Monsanto, GELVA®737), and then this mixture is cast to 0.6 mm thick onto the backing material—polyethylene film (3M-CoTran 9720) after settled to remove the air bubbles. The casting material is dried for 60 minutes at 45° C. and then the release liner is covered over the dried matrix. This formation is then cut into 20 cm$^2$ shape.

EXAMPLE 12

1.6 g of piroxicam is dissolved in 2.0 g of dimethylsulfoxide and 0.7 g of diethyleneglycol mono ethylether. 0.4 g of oleic acid, 0.1 g of propyleneglycol and 0.1 g of hydrocortisone are added to above solution and this solution is mixed well. This solution is mixed well with 15 g of polymer solution (Monsanto, GELVA®737), and then this mixture is settled to remove the air bubbles. The remaining steps are the same as set forth in Example 11.

EXAMPLE 13

2.0 g of piroxicam is dissolved in 2.0 g of dimethylsulfoxide and 0.7 g of diethyleneglycol mono ethylether. 0.4 g of oleic acid, 0.4 g of triethanolamine and 0.1 g of hydrocortisone are added to above solution and this solution is mixed well. This solution is mixed well with 15 g of polymer solution (Monsanto, GELVA®737), and then this mixture is settled to remove the air bubbles. The remaining steps are the same as set forth in Example 11.

EXAMPLE 14

1.2 g of piroxicam is dissolved in 1.8 g of dimethylsulfoxide and 0.5 g of diethyleneglycol mono ethylether. 0.4 g of oleic acid, 0.05 g of polysorbate 80 and 0.1 g of hydrocortisone are added to above solution and this solution is mixed well. This solution is mixed well with 15 g of polymer solution (Monsanto, GELVA®737), and then this mixture is settled to remove the air bubbles. The remaining steps are the same as set forth in Example 11.

EXAMPLE 15

1.2 g of piroxicam is dissolved in 1.8 g of dimethylsulfoxide and 0.5 g of diethyleneglycol mono ethylether. 0.5 g of glycolysed ethoxylated $C_8/C_{10}$ glycerides (Labrasol) is added to above solution and this solution is mixed well. This solution is mixed well with 10 g of polymer solution (Monsanto, GELVA®737), and then this mixture is settled to remove the air bubbles. The remaining steps are the same as set forth in Example 11.

EXPERIMENT 1

Anti-inflammatory activity on carrageenin-induced paw edema in rats.

Figure 3:
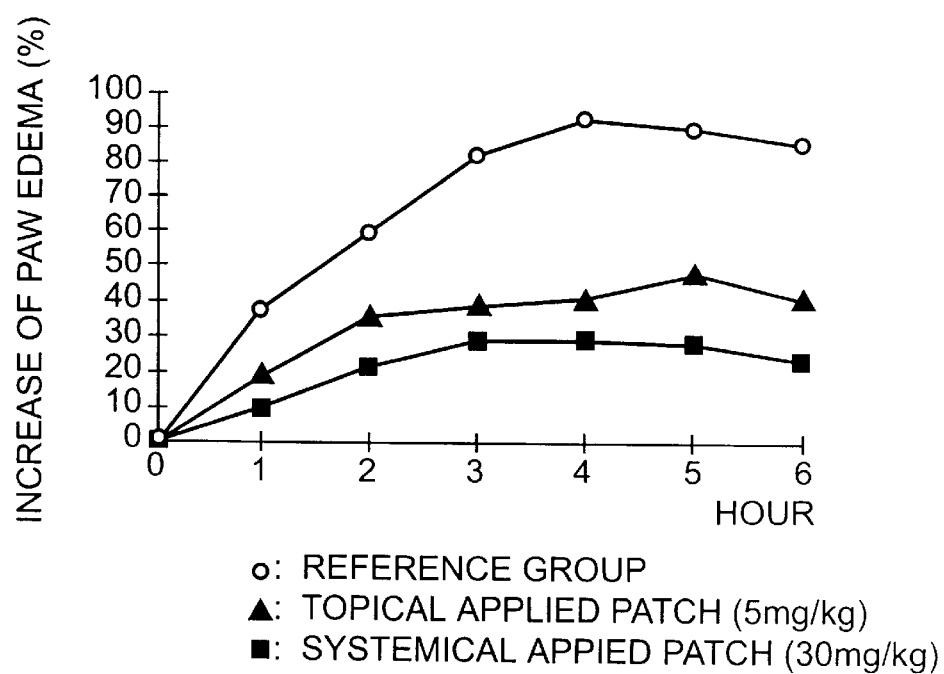
FIG. 3 is a graph illustrating the results of inhibition ratio on carrageenin-induced paw edema in rats.

Male rats of Wister strain, weighing 287±11 g (7~9 weeks old), were depilated and allowed to stand overnight for use in the experiment (Topical applied:5 mg/kg, systemical applied:30 mg/kg). Then, 0.1 ml of 1% carrageenin solution was hypodermally injected into left hind leg after 3 hours of applying patch. The swelling inhibition ratio is measured by plethysmometer (UGO BASILE TYPE 7150) at intervals of 1 hour for a 6 hours period after injection. The results are presented in FIG. 3.

EXPERIMENT 2

The flux of piroxicam through human skin is measured as following methods. In generally, the percutaneous flux is measured on nude mouse skin in vitro, but the flux on nude mouse skin is higher about 10 to 50 times than that of human skin. Thereof, it is impossible that the absolute value is calculated for the use of animal skin and in case of using human skin that is also different between in vitro and vivo.

In the present invention, in vitro test, human cadaver skin was obtained from Ohio Valley Tissue And Skin Center and hydrated for 24 hours with phosphate buffer (pH6.0 Standard buffer solution in U.S. Pharmacopoeia) before experiments. The hydrated skin was mouned in Frantz cell. The upper side of skin, having an available diffusion area of 1.0 cm$^2$, was exposed to ambient conditions. The lower side was filled by the receptor medium (5.0 ml, pH 6.0 Standard buffer solution in U.S. Phrmacopoeia) being stirred and kept at 32° C. Piroxicam patch directed in the present invention was adhered to upper side of skin and fixed with clamp. For 72 hours samples were withdrawn and replaced by fresh receptor medium keeping an infinite sink. The flux of piroxicam penetrating the skin was determined by measuring the concentration by HPLC system.

In vivo test, fifty male volunteers were subjected to residual test of patch.

Piroxicam patches, directed in the present invention, of which content was known were adhered to the outer side of volunteer's upper arm and maintained there for 72 hours, and then removed. The absorbed amount of piroxicam was determined by measuring the residual amount of piroxicam in removed patch by HPLC system.

<Measuring condition>

| | |
|---|---|
| Column: | $\mu$ Bondapak $C_{18}$ 3.9 mm (ID) 30 cm (L) |
| Mobile Phase: | 0.01M 1-heptane sulfonic acid, sodium salt/ Acetonitrile/Methanol (3:5:1) adjusted pH 3.0 with phosphoric acid |
| Dector: | UV (340 nm) |
| Injection volume: | 10 $\mu$l |
| Flow rate: | 1.0 ml/min |

The results are presented in Table 1.

TABLE 1

The Flux of Piroxicam through Human Skin.

|  | In vitro ($\mu g/cm^2 \cdot hr$) | In vivo ($\mu g/cm^2 \cdot hr$) |
|---|---|---|
| Example 7 | 3.52 | 0.72 |
| Example 8 | 6.10 | 0.82 |
| Example 9 | 11.28 | 1.78 |
| Example 10 | 15.79 | 2.55 |
| Example 12 | 34.32 | 5.20 |
| Example 14 | 30.23 | 4.58 |

As is seen from the above results, the flux of in vitro disclosed in U.S. patent application Ser. No. 925641 was a high value of 24. 0 $\mu g/cm^2$. hr in case of nude mouse skin but in case of human cadaver skin was a low value of 0.43 $\mu g/cm^2$. hr, while in the present invention was very higher 8 to 80 times than that in case of human cadaver skin. Also, the result in Japanese Patent Application Ser. No. 91-251534 was shown very lower value of 3.7 $\mu g/cm^2$. hr than in U.S. patent application Ser. No. 925641 in case of nude mouse skin.

EXPERIMENT 3

Fifty patients (30 male/20 female) were subjected to the systemical remedial effect test on patch in the present invention. The adhesion site of patch was same as that in Experiment 2. The results are presented in Table 2.

TABLE 2

The Remedial Effect of Piroxicam Patch.

| | Effect Responsibility (%) (male/female) | | | | |
|---|---|---|---|---|---|
| Age | -2 | -1 | 0 | +1 | +2 |
| 21–30 | — | — | 50/25 | 50/75 | — |
| 31–40 | — | — | 36/40 | 45/60 | 19/0 |
| 41–50 | — | — | 50/20 | 50/80 | — |
| 51–60 | — | — | 33/0 | 67/100 | — |
| 61– | — | 25/50 | 25/25 | 50/25 | — |
| Partial Average(M/F) | 0 | 3.3/10 | 40/25 | 50/65 | 6.7/0 |
| Total Average | 0 | 6.0 | 40.0 | 50.0 | 4.0 |

*Annotations
−2: more worse of symptoms,
−1: no change of symptoms
0: better of symptoms,
+1: very better of symptoms
+2: absent of symptoms

EXPERIMENT 4

Thirty male people were subjected to skin irritation test on effect of the existence of corticosteroid in piroxicam patch.

The patch was applied to te back of volunteers for 48 hours and the skin was evaluated for evidence of erythma, edema or more severe skin changes occurring 24, 48 and 72 hours after removal of patch. The results are presented in Table 3.

TABLE 3

Results of Skin Irritation

| | Time (hr) | | |
|---|---|---|---|
| Samples | 24 | 48 | 72 |
| Patch of Example 13 | 0 | 0 | 0 |
| Patch of Example 13 without hydrocortisone | 2 | 1 | 0 |
| Patch of Example 14 | 0 | 0 | 0 |
| Patch of Example 14 without hydrocortisone | 1 | 1 | 0 |

0: No extraodinary reaction
1: Slight erythma
2: Erythma or slight edema

What is claimed is:

1. A transdermal delivery matrix comprising:

(a) an active substance, wherein the weight of said active substance comprises 0.5–25% of the weight of said matrix, and wherein said active substance is piroxicam;

(b) an adhesive polymer, wherein said adhesive polymer comprises 35–90% of the weight of said matrix;

(c) an absorption assistant, wherein said absorption assistant comprises 9–40% of the weight of said matrix, and wherein said absorption assistant is selected from the group consisting of dimethylsulfoxide, [dimethylacetamide, dimethylformamide,] an alkanolamine, an alkylamine, diethyleneglycol monoethylether, and N-alkyl pyrrolidone; and (d) a penetration enhancer, wherein said penetration enhancer comprises 0.5–10% of the weight of said matrix, and wherein said penetration enhancer is selected from the group consisting of an alkylene glycol, a propylene glycol, [1-alkylazacycloheptane-2-one, 1-dodecylazacycloheptane-2-one,] lauric diethanolamide, oleic acid, and a polyethylene glycol.

2. The transdermal delivery matrix of claim 1, wherein said active substance further comprises an anti-inflammatory steroid.

3. The transdermal delivery matrix of claim 2, wherein said anti-inflammatory steroid comprises 0.5–15% of the weight of said matrix.

4. The transdermal delivery matrix of claim 2, wherein said anti-inflammatory steroid is selected from the group consisting of cortisone, hydrocortisone, prednisolone, and dexamethasone.

5. The transdermal delivery matrix of claim 4, wherein said anti-inflammatory steroid comprises 0.5–15% of the weight of said matrix.

6. The transdermal delivery matrix of claim 1, wherein said matrix comprises one or more laminated layers.

* * * * *